United States Patent
Ma et al.

(10) Patent No.: US 10,406,235 B2
(45) Date of Patent: Sep. 10, 2019

(54) USE OF MULTI-ARM POLYETHYLENE GLYCOL MODIFIER AND APPLICATION OF MULTI-ARM POLYETHYLENE GLYCOL MODIFIER IN L-ASPARAGINASUM MODIFICATION

(71) Applicants: ZONHON BIOPHARMA INSTITUTE INC., Changzhou, Jiangsu (CN); GENSUN INSTITUTE OF BIOMEDICINE CO., LTD., Wujin Changzhou, Jiangsu (CN)

(72) Inventors: Bruce Yong Ma, Jiangsu (CN); Jun Wang, Jiangsu (CN); Dinglong Wu, Jiangsu (CN); Chunlin Xu, Jiangsu (CN); Yaofang Wang, Jiangsu (CN)

(73) Assignees: ZONHON BIOPHARMA INSTITUTE INC., Changzhou (CN); GENSUN INSTITUTE OF BIOMEDICINE CO., LTD., Changzhou (CN)

( * ) Notice: Subject to any disclaimer, the term of this patent is extended or adjusted under 35 U.S.C. 154(b) by 124 days.

(21) Appl. No.: 15/109,304

(22) PCT Filed: Jul. 28, 2014

(86) PCT No.: PCT/CN2014/083143
§ 371 (c)(1),
(2) Date: Jun. 30, 2016

(87) PCT Pub. No.: WO2015/101033
PCT Pub. Date: Jul. 9, 2015

(65) Prior Publication Data
US 2017/0043028 A1    Feb. 16, 2017

(30) Foreign Application Priority Data

Dec. 30, 2013  (CN) .......................... 2013 1 0745273

(51) Int. Cl.
| | | |
|---|---|---|
| *A61K 38/43* | (2006.01) |
| *A61K 38/50* | (2006.01) |
| *A61K 47/60* | (2017.01) |
| *C12N 9/16* | (2006.01) |
| *C12N 9/82* | (2006.01) |
| *C12N 9/96* | (2006.01) |
| *A61K 47/48* | (2006.01) |
| *C12N 9/80* | (2006.01) |
| *A61K 9/00* | (2006.01) |
| *A61K 9/19* | (2006.01) |
| *A61K 38/44* | (2006.01) |
| *C12N 9/06* | (2006.01) |

(52) U.S. Cl.
CPC ...... *A61K 47/48215* (2013.01); *A61K 9/0019* (2013.01); *A61K 9/19* (2013.01); *A61K 38/44* (2013.01); *A61K 38/50* (2013.01); *A61K 47/60* (2017.08); *C12N 9/0016* (2013.01); *C12N 9/16* (2013.01); *C12N 9/80* (2013.01); *C12N 9/82* (2013.01); *C12N 9/96* (2013.01); *C12Y 104/01002* (2013.01); *C12Y 301/03001* (2013.01); *C12Y 305/01001* (2013.01); *C12Y 305/01005* (2013.01)

(58) Field of Classification Search
None
See application file for complete search history.

(56) References Cited

U.S. PATENT DOCUMENTS

2009/0118181 A1 * 5/2009 Walker ............. A61K 47/48215
514/8.4

FOREIGN PATENT DOCUMENTS

| CN | 1498965 A | 5/2004 |
|---|---|---|
| CN | 101082043 A | 12/2007 |
| CN | 101586099 A | * 11/2009 |
| CN | 101586099 A | 11/2009 |
| CN | 102573917 A | 7/2012 |

OTHER PUBLICATIONS

Creative PEGWorks, "4-Arm & 8-Arm PEG", Sep. 2012; https://web.archive.org/web/20120901081618/https://www.creativepegworks.com/multiarm_PEG.html; retrieved from Internet Archive Wayback Machine on Jan. 5, 2019 (Year: 2012).*
Enniish Abstract of CN 101586099 A.
English Abstract of CN 101082043 A.
English Abstract ofCN 102573917 A.
English Abstract of CN 1498965 A.

* cited by examiner

*Primary Examiner* — Michelle F. Paguio Frising
(74) *Attorney, Agent, or Firm* — Buchanan Ingersoll & Rooney PC

(57) ABSTRACT

Methods for use of a multi-arm polyethylene glycol (PEG) modifier in modification of asparaginase. The described multi-arm PEG modifier enhances the subunit interaction of a multimeric protein to maintain the multimeric protein in a polymerized form, thereby improving the stability of the multimeric protein, maintaining the bioactivity of the multimeric protein, and reducing the probability of exposure of the antigen binding site after depolymerization of the subunits, so as to reduce the immunogenicity.

19 Claims, 6 Drawing Sheets
(1 of 6 Drawing Sheet(s) Filed in Color)
Specification includes a Sequence Listing.

ND APPLICATION OF

SEQUENCE LISTING

```
<160> NUMBER OF SEQ ID NOS: 8

<210> SEQ ID NO 1
<211> LENGTH: 239
<212> TYPE: PRT
<213> ORGANISM: Sus scrofa

<400> SEQUENCE: 1

Ile Ile Gly Gly Arg Glu Cys Glu Lys Asp Ser His Pro Trp Gln Val
1               5                   10                  15

Ala Ile Tyr His Tyr Ser Ser Phe Gln Cys Gly Gly Val Leu Val Asp
            20                  25                  30

Pro Lys Trp Val Leu Thr Ala Ala His Cys Lys Asn Asp Asn Tyr Gln
        35                  40                  45

Val Trp Leu Gly Arg His Asn Leu Phe Glu Asn Glu Val Thr Ala Gln
```

```
                50                  55                  60
Phe Phe Gly Val Thr Ala Asp Phe Pro His Pro Gly Phe Asn Leu Ser
 65                  70                  75                  80

Leu Leu Lys Asn His Thr Lys Ala Asp Gly Lys Asp Tyr Ser His Asp
                 85                  90                  95

Leu Met Leu Leu Arg Leu Gln Ser Pro Ala Lys Ile Thr Asp Ala Val
                100                 105                 110

Lys Val Leu Glu Leu Pro Thr Gln Glu Pro Glu Leu Gly Ser Thr Cys
                115                 120                 125

Gln Ala Ser Gly Trp Gly Ser Ile Glu Pro Gly Pro Asp Asp Phe Glu
                130                 135                 140

Phe Pro Asp Glu Ile Gln Cys Val Glu Leu Thr Leu Leu Gln Asn Thr
145                 150                 155                 160

Phe Cys Ala Asp Ala His Pro Asp Lys Val Thr Glu Ser Met Leu Cys
                165                 170                 175

Ala Gly Tyr Leu Pro Gly Gly Lys Asp Thr Cys Met Gly Asp Ser Gly
                180                 185                 190

Gly Pro Leu Ile Cys Asn Gly Met Trp Gln Gly Ile Thr Ser Trp Gly
                195                 200                 205

His Thr Pro Cys Gly Ser Ala Asn Lys Pro Ser Ile Tyr Thr Lys Leu
                210                 215                 220

Ile Phe Tyr Leu Asp Trp Ile Asn Asp Thr Ile Thr Glu Asn Pro
225                 230                 235

<210> SEQ ID NO 2
<211> LENGTH: 238
<212> TYPE: PRT
<213> ORGANISM: Homo sapiens

<400> SEQUENCE: 2

Ile Val Gly Gly Trp Glu Cys Glu Gln His Ser Gln Pro Trp Gln Ala
 1               5                  10                  15

Ala Leu Tyr His Phe Ser Thr Phe Gln Cys Gly Gly Ile Leu Val His
                 20                  25                  30

Arg Gln Trp Val Leu Thr Ala Ala His Cys Ile Ser Asp Asn Tyr Gln
                 35                  40                  45

Leu Trp Leu Gly Arg His Asn Leu Phe Asp Asp Glu Asn Thr Ala Gln
 50                  55                  60

Phe Val His Val Ser Glu Ser Phe Pro His Pro Gly Phe Asn Met Ser
 65                  70                  75                  80

Leu Leu Glu Asn His Thr Arg Gln Ala Asp Glu Asp Tyr Ser His Asp
                 85                  90                  95

Leu Met Leu Leu Arg Leu Thr Glu Pro Ala Asp Thr Ile Thr Asp Ala
                100                 105                 110

Val Lys Val Val Glu Leu Pro Thr Gln Glu Pro Glu Val Gly Ser Thr
                115                 120                 125

Cys Leu Ala Ser Gly Trp Gly Ser Ile Glu Pro Glu Asn Phe Ser Phe
                130                 135                 140

Pro Asp Asp Leu Gln Cys Val Asp Leu Lys Ile Leu Pro Asn Asp Glu
145                 150                 155                 160

Cys Lys Lys Ala His Val Gln Lys Val Thr Asp Phe Met Leu Cys Val
                165                 170                 175

Gly His Leu Glu Gly Gly Lys Asp Thr Cys Val Gly Asp Ser Gly Gly
                180                 185                 190
```

```
Pro Leu Met Cys Asp Gly Val Leu Gln Gly Val Thr Ser Trp Gly Tyr
            195                 200                 205

Val Pro Cys Gly Thr Pro Asn Lys Pro Ser Val Ala Val Arg Val Leu
    210                 215                 220

Ser Tyr Val Lys Trp Ile Glu Asp Thr Ile Ala Glu Asn Ser
225                 230                 235
```

<210> SEQ ID NO 3
<211> LENGTH: 717
<212> TYPE: DNA
<213> ORGANISM: Homo sapiens

<400> SEQUENCE: 3

| | | | | | |
|---|---|---|---|---|---|
| atcgtcggtg | gatgggaatg | tgagcaacat | tctcagccat | ggcaagcagc | tttgtaccac | 60 |
| ttttccacct | tccagtgtgg | tggaattttg | gttcatagac | aatgggtcct | tactgccgca | 120 |
| cactgcatct | ctgataacta | tcagttgtgg | cttggtagac | ataacttgtt | tgatgacgaa | 180 |
| aatactgccc | aattcgttca | tgtctcagag | agttttccac | accctggttt | caacatgtct | 240 |
| ttgcttgaaa | atcatactag | acaggctgat | gaggactact | cccacgattt | gatgttgctt | 300 |
| agacttacag | aaccagccga | taccattact | gacgcagtta | aggttgtcga | gttgccaaca | 360 |
| caagaacctg | aggttggttc | aacctgtttg | gcttctggtt | ggggttctat | tgaaccagag | 420 |
| aactttagtt | tccctgatga | cttgcagtgt | gttgatttga | agatccttcc | taatgacgaa | 480 |
| tgcaagaaag | ctcatgttca | aaaagtcaca | gatttcatgt | tgtgtgttgg | tcaccttgaa | 540 |
| ggtggaaagg | atacctgtgt | tggagactct | ggtggaccat | tgatgtgcga | cggtgttctt | 600 |
| caaggagtca | cttcatgggg | ttatgttcct | tgcggaacac | caaacaagcc | tagtgtcgca | 660 |
| gttagagtcc | ttagttatgt | caagtggatc | gaagatacaa | tcgctgaaaa | tagttag | 717 |

<210> SEQ ID NO 4
<211> LENGTH: 717
<212> TYPE: DNA
<213> ORGANISM: Homo sapiens

<400> SEQUENCE: 4

| | | | | | |
|---|---|---|---|---|---|
| atcgtcgggg | gttgggagtg | tgaacagcat | agtcagccct | ggcaggccgc | tctgtaccac | 60 |
| ttctccacct | ttcagtgcgg | cggaatcctg | gtgcacaggc | agtgggtcct | gacagcagcc | 120 |
| cattgtatta | gcgataacta | tcagctgtgg | ctgggccggc | ataacctgtt | cgacgatgag | 180 |
| aataccgccc | agtttgtgca | cgtctcagaa | tccttccccc | atcctggctt | caacatgagt | 240 |
| ctgctggaga | tcacaccagc | caggctgac | gaagattact | cacatgacct | gatgctgctg | 300 |
| cgactgacag | agccagcaga | cactatcacc | gatgctgtga | aggtggtcga | gctgcccaca | 360 |
| caggaacctg | aagtgggctc | tacttgcctg | gcaagcggat | ggggttctat | cgagcctgaa | 420 |
| aacttcagtt | ttccagacga | tctgcagtgc | gtggacctga | agattctgcc | taatgatgag | 480 |
| tgtaagaaag | ctcacgtcca | gaaagtgact | gatttttatgc | tgtgcgtggg | gcatctggag | 540 |
| ggaggcaagg | acacctgcgt | cggcgactcc | ggaggacctc | tgatgtgtga | cggggtgctg | 600 |
| cagggtgtca | ctagctgggg | ctacgtgcca | tgtggaaccc | caaataagcc | ctccgtggcc | 660 |
| gtcagagtgc | tgagctatgt | gaaatggatc | gaggacacca | ttgctgaaaa | cagttga | 717 |

<210> SEQ ID NO 5
<211> LENGTH: 34
<212> TYPE: DNA
<213> ORGANISM: Artificial sequence
<220> FEATURE:

```
<223> OTHER INFORMATION: Synthetic oligonucleotide

<400> SEQUENCE: 5
gccgctcgag aagagagaag cagaggctat cgtc                              34

<210> SEQ ID NO 6
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 6
aaggaaaaaa gcggccgcct aactattttc agcgat                            36

<210> SEQ ID NO 7
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 7
catgcctagg gccaccatgt ccgctctgct                                   30

<210> SEQ ID NO 8
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 8
gggcgtatac tcaactgttt tcagcaatgg t                                 31
```

USE OF MULTI-ARM POLYETHYLENE GLYCOL MODIFIER AND APPLICATION OF MULTI-ARM POLYETHYLENE GLYCOL MODIFIER IN L-ASPARAGINASUM MODIFICATION

RELATED APPLICATION INFORMATION

This application is a 371 of International Application PCT/CN2014/083143 filed 28 Jul. 2014, which claims priority from Chinese Application No. 201310745273.4 filed 30 Dec. 2013, the content of which is incorporated herein by reference.

REFERENCE TO SEQUENCE LISTING SUBMITTED VIA EFS-WEB

This application includes an electronically submitted sequence listing in .txt format. The .txt file contains a sequence listing entitled "2016-10-31 U 019673-8 ST25" created on Oct. 31, 2016 and is 7,530 bytes in size. The sequence listing contained in this .txt file is part of the specification and is hereby incorporated by reference herein in its entirety.

FIELD OF THE INVENTION

The present invention relates to novel use of a multi-arm polyethylene glycol (PEG) modifier and use of the PEG modifier in asparaginase pegylation.

DESCRIPTION OF RELATED ART

Polyethylene glycol (PEG) is an uncharged linear polymer that can freely coil in a solution, is non-toxic and weakly antigenic, and has a good biocompatibility. Covalent modification of a protein with PEG (PEGylation) can increase the in-vivo circulation half-life, reduce the antigenicity, enhance the solubility, and alter the biodistribution in human of the protein. Since the initial report about the PEGylation by Abuchowski, Davis et al (J. Biol. Chem. 1977, 252:3578-3581.) in 1977, PEGylation is a well-established technology used extensively to transform proteins, peptides into more potent drugs than their corresponding unmodified native molecules. At present, the technology for protein PEGylation has become one of the most effective ways to reduce the immunogenicity and improve the pharmacokinetic/pharmacodynamic properties of protein drugs, and is approved by FDA for use with medicines, food, and cosmetics.

In most cases, as compared with unmodified original proteins, the activity of the PEGylated protein drugs is reduced, and is generally only 30-40% or even lower of that of the original proteins. For example, PEG-Intron available from the Schering-Plough Corporation is an interferon modified with PEG having a molecular weight of 5000, the activity of which after modification is only 8% of that of the original protein. In addition, the protein activity after modification generally decreases much considerably with increasing molecular weight of PEG. For example, the activity of erythropoietin (EPO) modified with PEG having a molecular weight of 20 kDa, 30 kDa, and 40 kDa decreases significantly with increasing molecular weight of PEG (Yinjue Wang, journal of controlled release, 2010 (145):306-313). Interferon-α-2a is modified by Bailon et al with a branched 40 kDa PEG, and the resultant mono-modified product has a long circulation half-life, but retains only 7% of the in-vitro activity (Bailon P, Bioconjugate Chem., 2001, 12:195-202.).

After decades of development, the technology of PEG modification is mature at present. However, there are no general-purpose PEG modifiers and modification methods available for modifying all the protein drugs. The protein structure, the molecular weight and shape of PEG used, and the site to be modified have a high influence on the bioactivity and therapeutical efficacy of the PEGylated proteins. For the modification of a particular drug, the PEG modifier is an important factor affecting the physical and chemical properties, in-vivo and in-vitro bioactivity, pharmacokinetics, pharmacodynamics, and clinical manifestations of the modified products. Therefore, the selection of the modifier (the type and molecular weight of the modifier) and the control of the modification play an important role in the technology of PEG modification. The pharmacokinetic behavior of a natural protein cannot be precisely predicted by the analysis of protein structure, and the prediction for the pharmacokinetic behavior of a PEG conjugate becomes even less feasible after PEG is conjugated to a protein, because numerous new variables such as molecular weight and the type of the modifier are introduced. In this regard, optimum solutions are determined for various protein drugs by selecting different types of modifiers and different molecular weights of modifiers and by detection of physical and chemical properties and evaluation with animal experiments.

Multimeric protein (oligomeric or polymeric protein) refers to a polymer formed of two or more independent subunits through intermolecular interaction. Each subunit is generally composed of one peptide chain, or sometimes two or more peptide chains connected by a disulfide bond. Each subunit is folded per se to have a spatial conformation, and different subunits are integrated together by virtue of hydrophobic interaction, hydrogen bonding, ionic bonding and interaction, to form the quaternary structure of a protein, and form an entity having biochemical activities. In the nature, there are numerous multimeric proteins in the whole protein family. For example, the alkaline phosphatase is composed of two subunits, in which the molecular weight of each subunit is about 28 kDa, and the molecular weight of the whole molecule is about 56 kDa. The human tumor necrosis factor is composed of three subunits, in which the molecular weight of each subunit is about 17 kDa, and the molecular weight of the whole molecule is about 51 kDa. An active form of L-asparaginase is a homologous tetramer formed of 4 subunits, in which each subunit comprises 326 amino acids, and the molecular weight of the whole protein molecule is about 140 kDa. The monomeric Hp urease is a hexamer composed of the subunits A and B, in which the molecular weights of the subunits A and B are about 30 kDa and 64 kDa respectively, and the ratio is 1:1. The bioactivity of a multimeric protein generally correlates with the structure of the polymer. The human tumor necrosis factor TNF-α has the highest bioactivity when in the form of a trimer, which is 8 times of the activity of each subunit present alone. L-asparaginase has a corresponding bioactivity only in the form of a homologous tetramer formed of 4 subunits. In addition, after depolymerization, the activity of the multimeric protein is generally dramatically reduced, and more epitopes tend to be exposed after degradation in-vivo when the multimeric protein is used as a drug, such that an immune response is induced, thereby reducing the therapeutic effect and causing adverse effect. Therefore, how to prevent the depolymerization of the subunits is critical to maintain the bioactivity of the multimeric protein.

The proteins having L-asparagine aminohydrolase activity (generally referred to as L-asparaginase, L-asparaginase, or asparaginase) are effective in treatment of acute lymphoblastic leukemia (ALL) in children or adults. In recent years, the drugs containing L-asparaginase are used in combination with chemotherapy to treat NK/T cell lymphoma, and a good therapeutic effect is achieved. The NK/T cell lymphoma is a special non-Hodgkin lymphoma, which is frequently found in Asia and Latin America, and the incidence is relatively high in China. Depending on the tumor position, the NK/T cell lymphoma may include nasal NK/T cell lymphoma and non-nasal NK/T cell lymphoma.

Moreover, the L-asparaginase is also used to treat Hodgkin's disease, acute myeloid leukemia, acute myelomonocytic leukemia, chronic lymphocytic leukemia, lymphosarcoma, reticulum cell sarcoma and melanotic sarcoma (Kotzia and labrou, J. Biotechnol. 127 (2007) 657-669). An active form of L-asparaginase is a homologous tetramer formed of 4 subunits, in which each subunit comprises 326 amino acids. The L-asparaginase is initially purified from several organisms, including *E. coli* and *Erwinia carotovora*. For the mammalians, the L-asparaginase is found only in slightly more than trace amount in guinea pig (superfamily Cavioidea) and some platyrrhinians (New World monkey). However, the L-asparaginase is a foreign protein having a high immunogenicity for human since it is derived from exogenous organisms, and limited in use in clinic due to the commonly occurred progressive immune reaction and systemic anaphylaxis in clinic (ZHANG Lina, and GONG Daohua. Jiangsu Medical Journal. Toxic side effect in treatment of childhood acute lymphocytic leukemia with L-Asparaginase. 2005, 31(5):392; and WANG Ningling, and LIU Zhizhang, et al. Toxic side effect in treatment of childhood leukemia with L-Asparaginase and control thereof. Journal of China Pediatric Blood, 2005, 10(3):133).

At present, PEG modification of L-Asparaginase is extensively researched. The PEG modified L-asparaginase product Oncaspar (Enzoninc) became available as early as in 1994, and was approved in 2006 as the first line treatment for ALL in children and adults. However, PEG used in Oncaspar is succinimidyl succinate-PEG (SS-PEG) having an ester bond that is susceptible to enzymatic hydrolysis, and is labile at a slightly basic pH (U.S. Pat. No. 4,670,417), which greatly reduces the in-vitro and in-vivo stability and causes a high adverse effect. The PEG modified L-asparaginase marketed in China is exclusively "Pegaspargase" manufactured by Hengrui Medicine Co., Ltd., which is a generic drug of Oncaspar, and also suffers from the problem of tendency to degradation of PEG.

Related patents granted in China include "Method for preparing PEG modified Asparaginase" (Application No. 02149328.6) issued to Lianyungang Xinyang Pharmaceutical Co., Ltd, and "PEG modified L-Asparaginase" (Application No. 200610027026.0) issued to Shanghai Institute of Pharmaceutical Industry. The modification method used in the patent issued to Lianyungang Xinyang Pharmaceutical Co., Ltd is a two-step reaction process, in which the modification is firstly carried out with a low molecular weight PEG modifier, followed by secondary modification with a high molecular weight PEG modifier. Such a modification method has troublesome steps, the uniformity of the modified product is difficult to control, and the purification is complex. The PEG modifier used in the patent issued to Shanghai Institute of Pharmaceutical Industry is unlikely to hydrolyze after binding to asparaginase; however, the activity loss is great after modification, and only 60% of the original activity of the protein is retained. A patent concerning PEG modified L-asparaginase is filed by the Arritz Pharmaceutical Co., Ltd recently. In the patent, the PEG modifier used is a commonly used modifier with which the amino group is modified at random, and the L-asparaginase modified is *Erwinia carotovora* derived. Several papers regarding PEG modified L-asparaginase are also published, in which a conventional monomethoxy PEG modifier is used. Compared with the unmodified original protein, although the immunogenicity of the PEG modified L-asparaginase provided in all the patents and literatures is reduced, the immunogenicity related problem still exists. Moreover, the problem of depolymerization of subunits in a multimeric protein is not addressed in all the patents and literatures.

SUMMARY OF THE INVENTION

In order to overcome the above technical problems existing in the prior art, an objective of the present invention is to provide use of a multi-arm PEG modifier in modification of a multimeric protein.

The PEG modifier is preferably conjugated to an amino group of the multimeric protein.

Preferably, the PEG modifier used in the present invention is an aldehyde or ester activated 4 to 8-arm PEG modifier and preferably a 4-arm PEG modifier.

More preferably, the multi-arm PEG modifier used in the present invention has a structure represented by Formula (I) or (II):

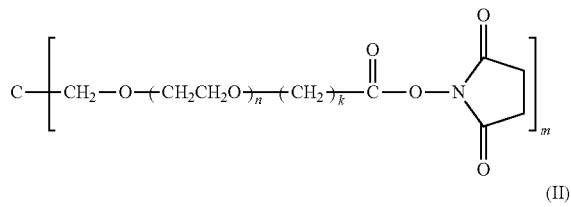

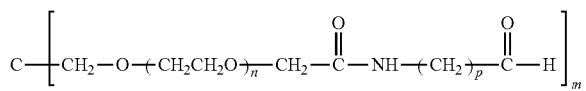

in which n is an integer ranging from 1 to 2000, preferably an integer ranging from 2 to 500, and more preferably an integer ranging from 25 to 100; k is 1 or 2, and preferably 1; m is an integer ranging from 2 to 16, and preferably 4; p is an integer ranging from 1 to 4, and preferably 2; and the molecular weight of the PEG modifier is from 1 to 100 kDa, preferably 1 to 40 kDa, and more preferably 5 to 10 kDa.

More preferably, the ester activated PEG modifier is 4-arm PEG succinimidyl acetate (4ARM-SCM), 4-arm PEG succinimidyl propionate (4ARM-SPA) or 4-arm PEG succinimidyl carbonate (4ARM-SC), and most preferably 4-arm PEG succinimidyl acetate (4ARM-SCM).

The aldehyde activated PEG modifier is 4-arm PEG propionaldehyde (4ARM-PALD), 4-arm PEG butyraldehyde (4ARM-BALD), 4-arm PEG acetaldehyde (4ARM-ALD) or 4-arm PEG amylic aldehyde (4ARM-AALD), and most preferably 4-arm PEG propionaldehyde.

Depending on the degree of polymerization, the molecule of the PEG modifier may be any molecule with a molecular weight of 2 to 40 kDa, and preferably a PEG molecule with a molecular weight of 5 kDa. The used multi-arm PEG preferably has, without limitation, the above structural formula.

The multimeric protein includes, but is not limited to, L-asparaginase, alkaline phosphatase, urease, and glutamate dehydrogenase.

Another objective of the present invention is to provide a method for preparing a PEGylated multimeric protein, which comprises the steps of:
(1) mixing a multimeric protein to be modified and a multi-arm PEG modifier at a molar ratio of 1:5-1:200, and subjecting them to modification in a buffer after mixing;
(2) after the modification is completed, removing the multi-arm PEG modifier in the modified product that is unreacted with the protein by ion exchange chromatography; and
(3) purifying the modified product by gel filtration chromatography, to collect the modified product of interest.

The multi-arm PEG modifier and the multimeric protein used are as described above.

Preferably, when the multi-arm PEG modifier is a propionaldehyde activated multi-arm PEG, the buffer has a pH ranging from about 5.0 to 6.0.

Preferably, when the multi-arm PEG modifier is a succinimidyl acetate activated multi-arm PEG, the buffer has a pH ranging from about 7.0 to 8.0.

Preferably, the modification in the step (1) is carried out with a protein concentration of 3 to 15 mg/mL.

Another objective of the present invention is to provide a multimeric protein modified with a multi-arm PEG. The multi-arm PEG modifier is preferably conjugated to an amino group of the multimeric protein.

The multi-arm PEG modifier and the multimeric protein used are as described above.

A fourth objective of the present invention is to provide a pharmaceutical composition comprising a multimeric protein modified with a multi-arm PEG or a pharmaceutically acceptable salt thereof, and a pharmaceutically acceptable adjuvant.

Preferably, the pharmaceutical composition is an injectable lyophilized powder. The adjuvant includes a pharmaceutically acceptable carrier and/or excipient.

Preferably, the multimeric protein modified with a multi-arm PEG and the pharmaceutical composition thereof are administered by intramuscular, intravenous or subcutaneous route.

The pharmaceutically acceptable salts are nontoxic when present in the administered amount and concentration. Such salts are prepared to promote the administration of the drugs by altering the physical properties of the compound without affecting the exertion of the physiological effect. The useful changes in physical properties include reduction of the melting point to promote transmucosal administration and increase of the solubility to facilitate the administration of a high concentration of drugs.

The pharmaceutically acceptable salt includes acid addition salts, such as sulfate, hydrochloride, fumarate, maleate, phosphate, acetate, citrate, lactate, tartarate, mesylate, benzene sulfonate, and others. The pharmaceutically acceptable salt may be derived from an acid, including hydrochloric acid, maleic acid, sulfuric acid, phosphoric acid, acetic acid, citric acid, lactic acid, tartaric acid, and others.

A pharmaceutically acceptable carrier and/or excipient may be blended into the pharmaceutical composition according to the present invention to facilitate the administration of a particular asparaginase. The carrier useful in practice of the present invention includes calcium carbonate, calcium phosphate, various sugars (e.g. lactose, glucose, and sucrose) or starch, cellulose derivatives, gelatin, vegetable oil, PEG and physiologically compatible solvents (including sterile water solution, salt solutions and dextran for injection).

A fifth objective of the present invention is to provide an asparaginase modified with a multi-arm PEG. The PEG is preferably conjugated to an amino group of the multimeric protein. The multi-arm PEG used is as described above.

The present invention further provides use of a L-asparaginase modified with a multi-arm PEG in the treatment of acute leukemia.

Advantageous Effect

In the present invention, it is found through research by the applicants that the depolymerization of the subunits in the multimeric protein is mainly caused by the easy in-vivo degradation because the advanced structure of the protein is maintained by the non-covalent interaction between the subunits, which is not as stable as the covalent bond, and more epitopes on the subunits are exposed after depolymerization, causing a high immunogenicity. The solution to this problem is to enhance the interaction between the subunits without or with little influence on the protein activity. Therefore, PEG modification is contemplated. However, it is obvious that the interaction between the subunits cannot be enhanced by the commonly used monomethoxy PEG modifier at present. Accordingly, there is a need for a modifier that can be conjugated to the protein and enhance the interaction between the subunits. After the interaction between the subunits is enhanced, the degradation cannot occur easily in vivo, and thus the epitopes will not be exposed to bring about the problem of immunogenicity. The multi-arm PEG modifier of the present invention can exactly satisfy the requirement, and is characterized by a plurality of activating groups on one PEG molecule that can react with the amino acid residues on the protein. Although the multi-arm PEG modifier used in the present invention is an existing PEG modifier, there is no report in literatures before the present invention about use of the multi-arm PEG modifier to modify a multimeric protein, to solve the problems of reduced stability, deactivation and increased immunogenicity resulting from depolymerization of the subunits in the multimeric protein.

Moreover, it is confirmed through experiments that compared with an original protein or a multimeric protein modified with a common PEG, multiple subunits in a multimeric protein modified with the multi-arm PEG provided in the present invention are better conjugated, whereby the depolymerization of the subunits is effectively prevented and the stability is much better. For example, compared with the L-asparaginase, alkaline phosphatase and urease which are unmodified or modified with a common PEG modifier, the L-asparaginase, alkaline phosphatase and urease modified with the multi-arm PEG provided in the present invention has a better stability and capability to retain the bioactivity, as well as stable and uniform structure. Compared with the commercially available PEGylated asparaginase product "Pegaspargase", the PEG modified asparaginase prepared in the present invention has a low immunogenicity, a good stability and uneasy detachment of PEG. Moreover, the asparaginase modified with the multi-arm PEG provided in the present invention further retains a high bioactivity, and has an obviously extended half-life and a stable and uniform structure.

At present, there is report in literatures about treatment of NK/T cell lymphoma with Pegaspargase in combination with chemotherapy, and a good therapeutic effect is achieved. Pegaspargase is a product obtained by modifying *E. Coli* derived L-asparaginase with PEG. The PEG modified L-asparaginase provided in the present invention is also *E. Coli* derived, and thus has a therapeutic effect similar to that of Pegaspargase. That is to say, the L-asparaginase modified with the multi-arm PEG provided in the present invention is useful in the treatment of NK/T cell lymphoma in combination with other chemotherapeutic agents.

The protein electrophoresis pattern of ASP modified with various PEGs is shown, in which the proteins in Lanes 1-6 are a protein Marker, Pegaspargase, 4SCM5K-ASP, 8SCM10K-ASP, 4PALD5K-ASP, and 4PALD1OK-ASP respectively. It can be seen from the result of protein electrophoresis that the molecular weight of Pegaspargase is diffuse, and the molecular weight of the PEG-ASP conjugates prepared with a multi-arm PEG modifier is uniform. Therefore, the conjugates prepared with a multi-arm PEG modifier have a uniformity that is obviously advantageous over the sample modified with a monomethoxy PEG modifier.

Figures 2A, 2B:
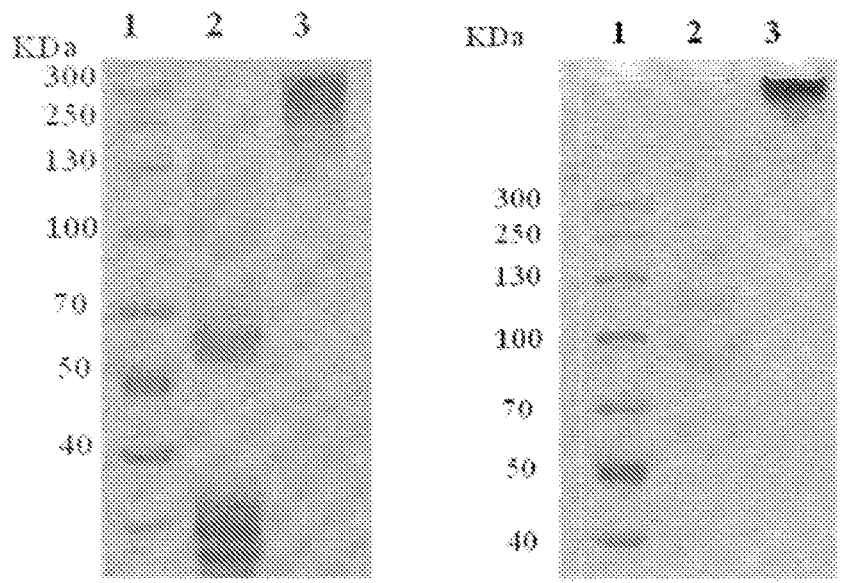
Figure 2C:
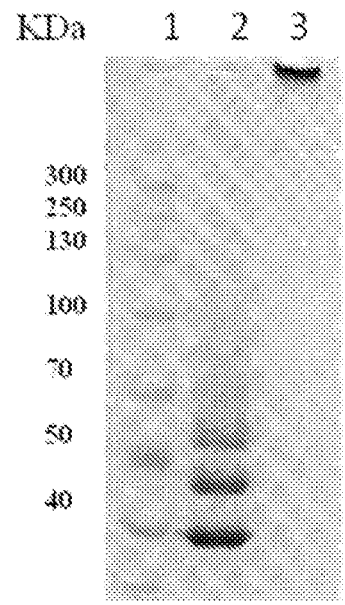

FIGS. 2a-2c show a protein electrophoresis pattern of AKP, URE, and GDH modified with various PEGs.

In FIG. 2a, the samples in Lanes 1-3 are a protein Marker, SCM5K-AKP, and 4SCM5K-AKP respectively. In FIG. 2b, the samples in Lanes 1-3 are a protein Marker, SCM5K-URE, and 4SCM5K-URE respectively. In FIG. 2c, the samples in Lanes 1-3 are a protein Marker, SCM5K-GDH, and 4SCM5K-GDH respectively. It can be seen from the result of protein electrophoresis that the active structure of the multimeric protein can be stabilized by modifying with a multi-arm PEG modifier, and the conjugate sample modified with a multi-arm PEG is much more uniform. Therefore, compared with a conventional monomethoxy PEG modifier, the molecular weight of the multimeric protein modified with a multi-arm PEG modifier is more uniform, and the conjugate has a better uniformity.

Figure 3A:
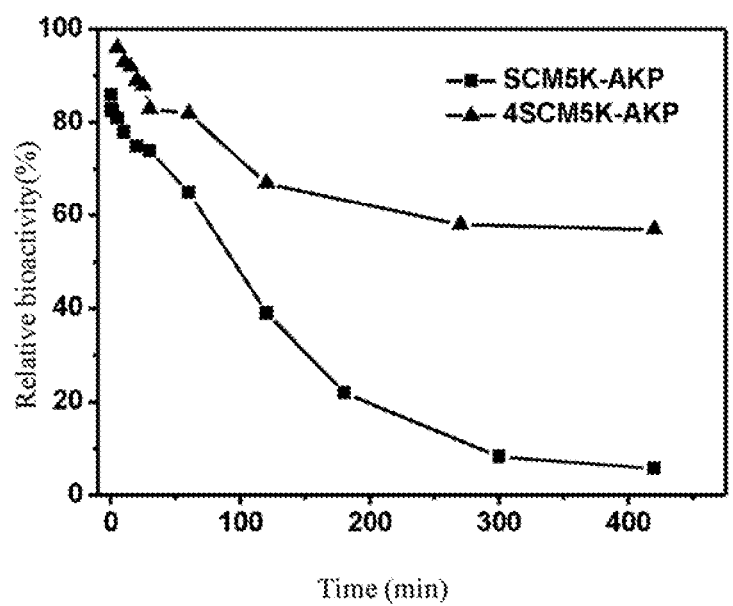
Figure 3B:
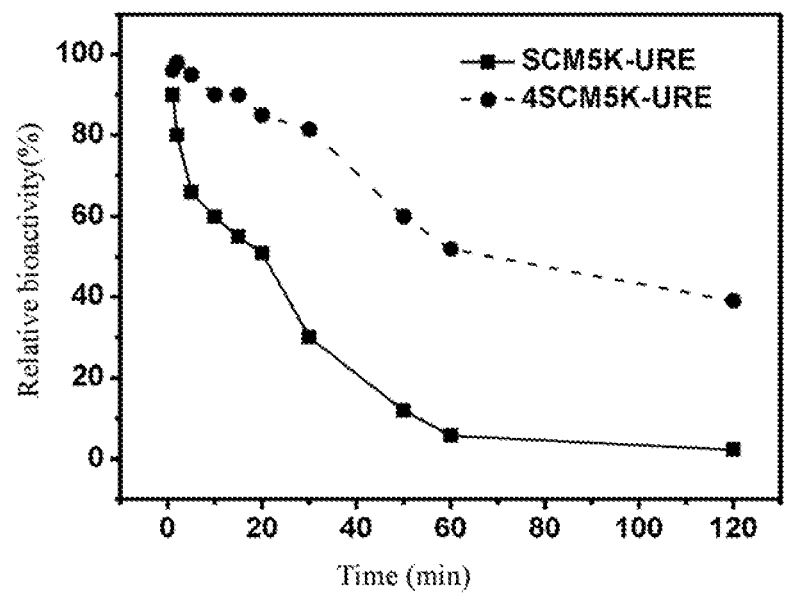
Figure 3C:
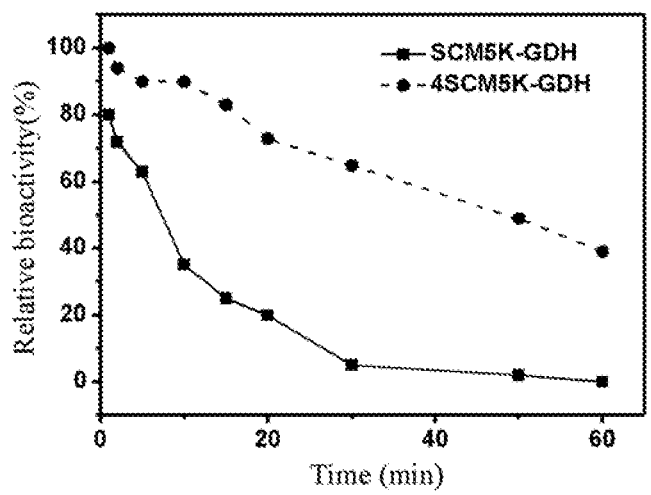

FIGS. 3a-3c show thermal stability study of PEG-AKP, PEG-URE, and PEG-GDH conjugates.

The stability of PEG-AKP, PEG-URE, and PEG-GDH conjugates are evaluated by determining variations in activity at different times in a water bath at 60° C. FIG. 3a shows the test results of SCM5K-AKP and 4SCM5K-AKP. The results show that the activity of SCM5K-AKP declines considerably in 2 hrs, and is substantially completely lost after 5 hrs; and the activity of 4SCM5K-AKP declines slowly during the test, with 60% of the original activity retained after 5 hrs. FIG. 3b shows the test results of SCM5K-URE and 4SCM5K-URE. The results show that the activity of SCM5K-URE is substantially lost in 1 hr, and 40% of the original activity of 4SCM5K-URE is retained after 2 hrs. A similar comparable experiment is also conducted. The SCM5K-GDH and 4SCM5K-GDH are sampled at 0.5 hr to detect the activity. The results in FIG. 3c show that the activity of SCM5K-GDH is substantially lost in 0.5 hr, and 65% of the original activity of 4SCM10K-GDH is retained at 0.5 hr. Therefore, compared with a conventional monomethoxy PEG modifier, the stability of the multimeric protein can be significantly improved by the multi-arm PEG modifier.

Figure 4:
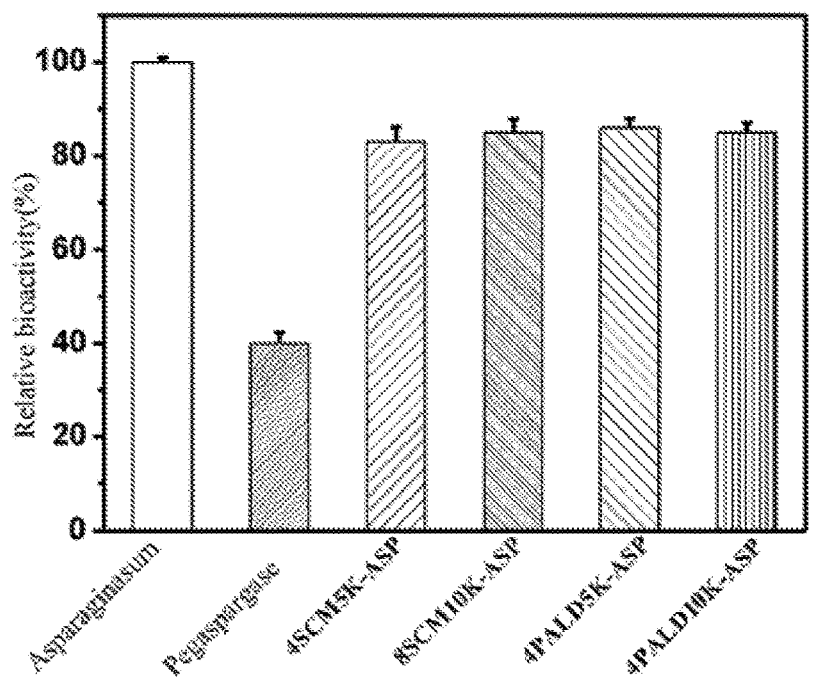

FIG. 4 shows in-vitro bioactivity of various PEG-ASP conjugates.

The in-vitro bioactivities of various PEG-ASP conjugates are compared. The bioactivity test results show that the activity of Pegaspargase is low, and is only 40% of the original protein; and the modified products 4SCM5K-ASP, 8SCM10K-ASP, 4PALD5K-ASP, and 4PALD10K-ASP have a high activity, with 80% of the activity of the original protein retained.

Figure 5:
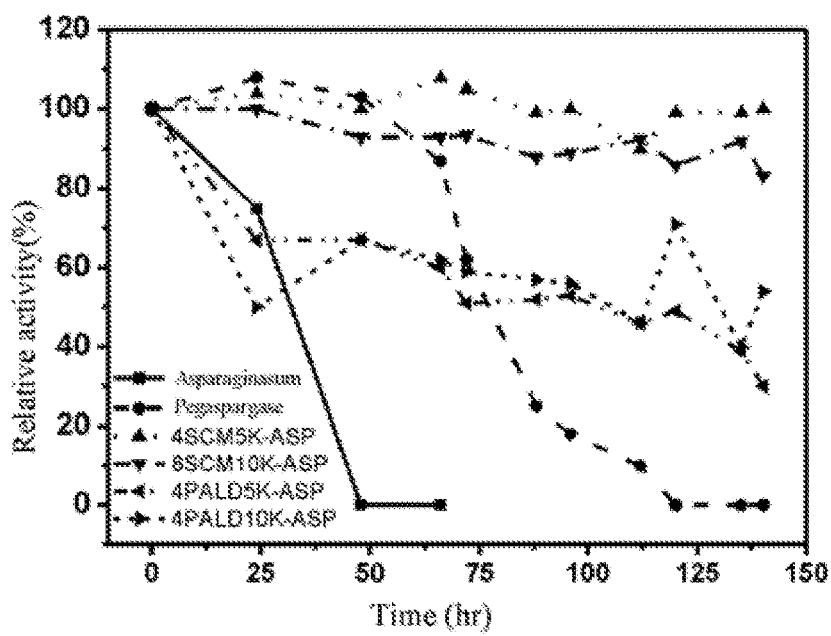

FIG. 5 shows stability study of various PEG-ASP conjugates.

The stability of various PEG-ASP conjugates at 37° C. are compared, and compared with Pegaspargase. The stability analysis results show that the 4SCM5K-ASP and 8SCM10K-ASP have a high stability and substantially no decrease of activity. The activity of 4PALD5K-ASP and 4PALD10K-ASP is greatly reduced, but still higher than that of Pegaspargase.

Figure 6A:
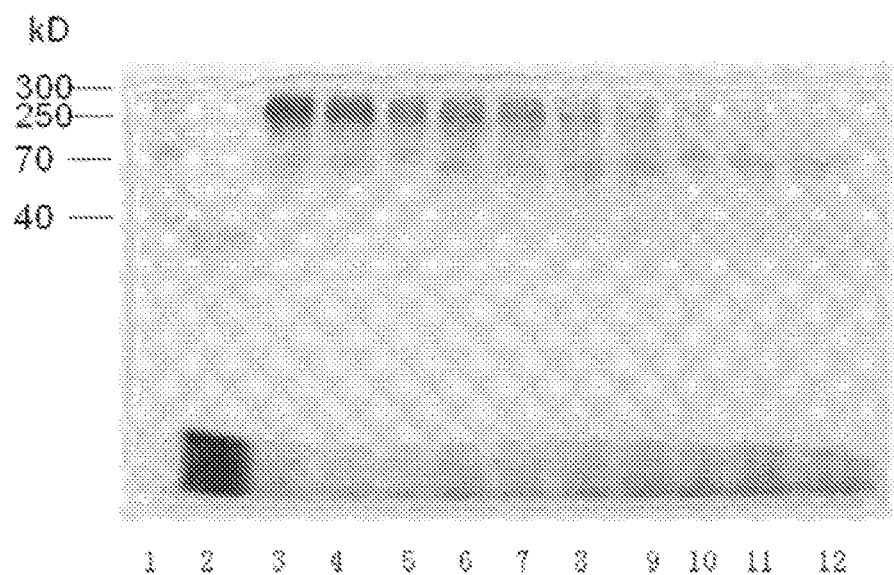
Figure 6B:
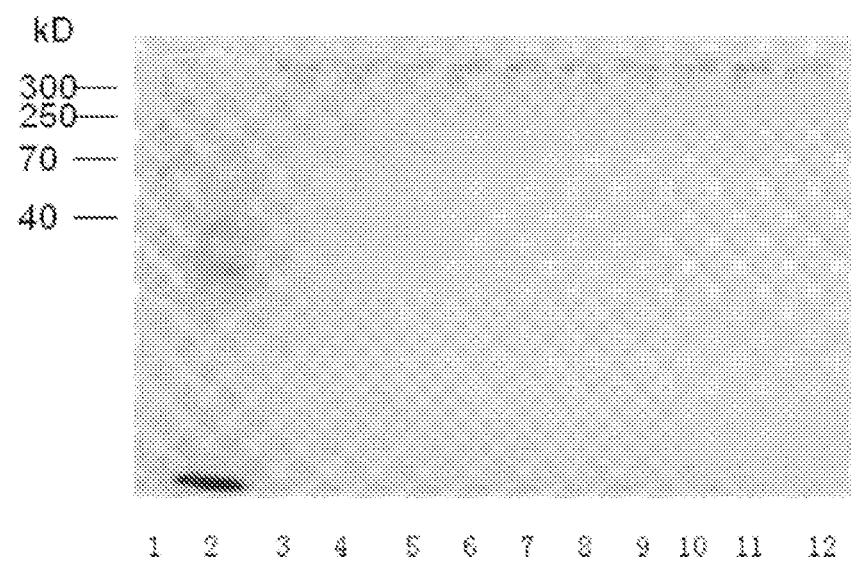

FIGS. 6a-6c show results of PEG-protein electrophoresis and iodine staining of PEG-ASP conjugate and Pegaspargase.

The detachment of PEG from the conjugate is detected by iodine staining after protein electrophoresis. FIG. 6a shows a protein electrophoresis pattern of Pegaspargase after standing in a water bath at 37° C. for different periods of time. Lane 1 is a protein Marker, Lane 2 is a monomethoxy PEG with a molecular weight of 5000, and Lanes 3-12 are respectively protein electrophoresis patterns of Pegaspargase after standing in a water bath at 37° C. for 0 hr, 12 hrs, 24 hrs, 36 hrs, 48 hrs, 60 hrs, 72 hrs, 84 hrs, 96 hrs, and 108 hrs. FIG. 6b shows a protein electrophoresis pattern of 4SCM5K-ASP after standing in a water bath at 37° C. for different periods of time. Lane 1 is a protein Marker, Lane 2 is 4SCM5K, and Lanes 3-12 are respectively protein electrophoresis patterns of 4SCM5K-ASP after standing in a water bath at 37° C. for 0 hr, 12 hrs, 24 hrs, 36 hrs, 48 hrs, 60 hrs, 72 hrs, 84 hrs, 96 hrs, and 108 hrs.

The results from comparison of the two figures show that the stability of Pegaspargase is poor, and the detachment of PEG is obvious and further exacerbated with the elapse of time. No detachment of PEG is observed for 4SCM5K-ASP in 108 hrs.

Figure 7A:
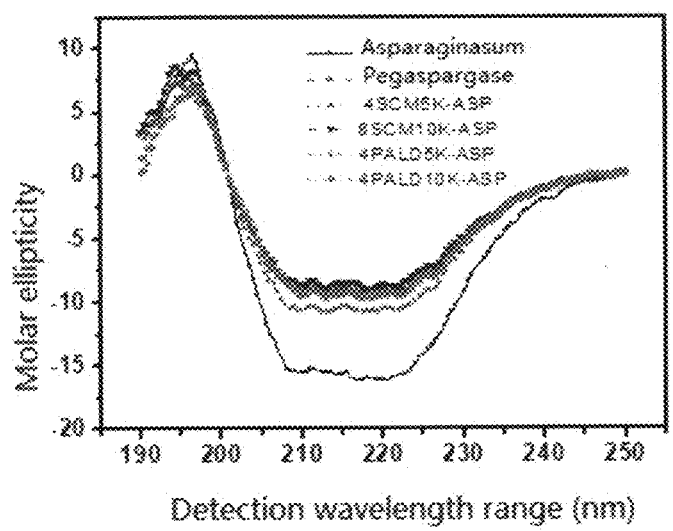
Figure 7B:
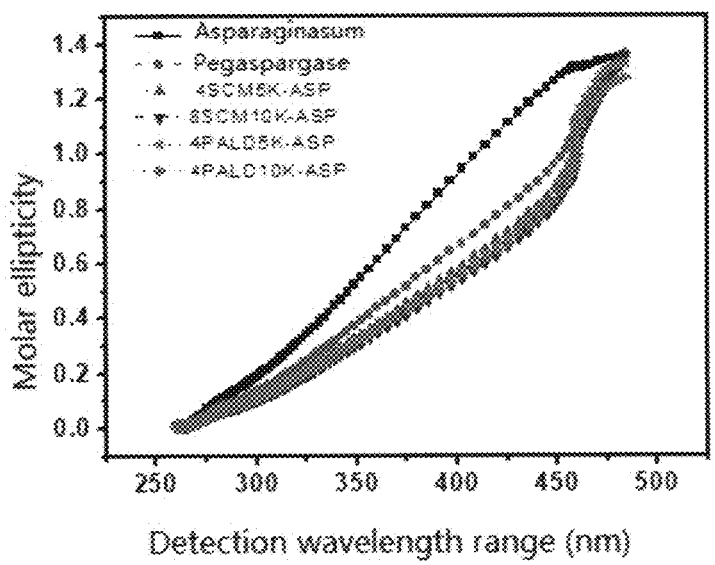

FIGS. 7a-7b compare circular dichroism spectra of various PEG-ASP conjugates with original protein.

FIG. 7a shows circular dichroism spectra of PEG-ASP conjugates in a far ultraviolet region, and FIG. 7b shows circular dichroism spectra of PEG-ASP conjugates in a near ultraviolet region.

The circular dichroism spectra of the PEG-ASP conjugates and the original protein are compared, to determine their differences in structure. It can be seen from the circular dichroism spectra that similar to Pegaspargase, the circular dichroism spectra in a far ultraviolet region and a near ultraviolet region of ASP after modification with various multi-arm PEGs substantially have no change, suggesting that no change occurs to the secondary and tertiary structure of ASP after modification.

FIG. 8 compares the therapeutic efficacy of various PEG-ASP conjugates. The therapeutic efficacy of various PEG-ASP conjugates are compared, and compared with that of the original protein and Pegaspargase. The pharmacodynamic test shows that 4SCM10K-ASP and 4PALD10K-ASP have a better inhibitory effect on tumor cells than Pegaspargase.

FIG. 9 shows immunogenicity of various PEG-ASP conjugates.

The immunogenicity of various PEG-ASP conjugates is compared and compared with that of the original protein and Pegaspargase. It can be seen from the result that the antibody titer resulting from 4SCM5K-ASP and 4PALD10K-ASP is lower than that resulting from the original protein and Pegaspargase.

DETAILED DESCRIPTION OF THE INVENTION

Definitions

The abbreviations used in the present invention have the following meanings:

PEG, polyethylene glycol, PEG modifier, polyethylene glycol modifier, and multi-arm polyethylene glycol modifier are polyethylene glycol molecules containing two or more activating groups.

Polyethylene glycol (PEG, HO—($CH_2CH_2O$)—$CH_2CH_2OH$) is a linear polymer bearing a hydroxyl group at two ends, which is formed through polymerization of ethylene oxide and composed of repeated oxyethylene, and may be branched, linear or multi armed. PEG is also referred to as poly (ethyleneoxide) (PEO), poly (oxy-ethylene) (POE), or polyoxirane. In general, the term PEG is used when the molecular weight is less than 20,000, and the term PEO is used when the molecular weight is higher. The ordinary PEG has a hydroxyl group respectively at two ends, and methoxy PEG (mPEG) is obtained if the PEG is capped with a methyl group at one end, which is frequently used in PEGylation of proteins.

Polyethylene glycol modifier refers to a functionalized PEG derivative which is activated polyethylene glycol mainly used in modification of protein and polypeptide drugs, and is also referred to as modified polyethylene glycol or modified PEG.

4SCM5K is 4-arm PEG succinimidyl acetate with a molecular weight of 5 k Da.

8SCM10K is 8-arm PEG succinimidyl acetate with a molecular weight of 10 kDa.

4SCM10K is 4-arm PEG succinimidyl acetate with a molecular weight of 10 kDa.

4PALD5K is 4-arm PEG propionaldehyde with a molecular weight of 5 kDa.

4PALD10K is 4-arm PEG propionaldehyde with a molecular weight of 10 kDa.

SCM5K is monomethoxy PEG succinimidyl acetate with a molecular weight of 5 kDa.

AKP is alkaline phosphatase; ASP is asparaginase; URE is urease; and GDH is glutamate dehydrogenase.

As used in this application, the term "conjugate" refers to a product obtained by modifying a multimeric protein such as asparaginase or urease with PEG.

Several products obtained by modifying asparaginase with PEGs are referred to herein as "4SCM5K-ASP, 8SCM10K-ASP, 4PALD5K-ASP, or 4PALD10K-ASP", or may be collectively referred to as PEG-ASP or PEG modified ASP conjugates. The products obtained by modifying alkaline phosphatase with PEG are referred to herein as "4SCM5K-AKP or SCM5K-AKP" or may be collectively referred to as PEG-AKP or PEG modified AKP conjugate. The products obtained by modifying urease with PEG are referred to herein as "4SCM5K-URE or SCM5K-URE" or may be collectively referred to as PEG-URE or PEG modified URE conjugate. The products obtained by modifying glutamate dehydrogenase with PEG are referred to herein as "4SCM5K-GDH or SCM5K-GDH" or may be collectively referred to as PEG-GDH or PEG modified GDH conjugate.

The PEG modifier of the present invention preferably has a molecular weight ranging from about 2 kDa to about 40 kDa. More specifically, the PEG modifier has a molecular weight selected from 2 kDa, 5 kDa, and 10 kDa. In a particular embodiment, the molecular weight of the PEG modifier is 5 kDa or 10 kDa.

The PEG modifier used in the present invention is preferably an aldehyde or ester activated PEG. Specifically, the PEG modifier is propionaldehyde or succinimidyl acetate activated PEG.

In the present invention, the protein modified may be a multimeric protein of any source. In a particular embodiment, the multimeric protein modified is alkaline phosphatase or urease. In a particular embodiment, the multimeric protein modified is asparaginase, which may be derived, cloned or produced from any source, including, for example, from animals, or via recombinant DNA technology, or any combination thereof.

For example, asparaginase may be extracted, without limitation, from *E. Coli*. In a specific conjugate embodiment of the present invention, the asparaginase has a sequence that is at least about 60% identical to that of the protein as shown in SEQ ID NO: 1, and more particularly at least about 65%, 70%, 75%, 80%, 85%, 90%, 91%, 92%, 93%, 94%, 95%, 96%, 97%, 98% or 100% identical to that of the protein as shown in SEQ ID NO:1.

In a particular embodiment, the protein is asparaginase derived from *E. Coli*, which has the sequence as shown in SEQ ID NO: 1.

A fragment of the protein as shown in SEQ ID NO:1 is also included in the definition of the protein used in the conjugate of the present invention. The "fragment of the protein as shown in SEQ ID NO: 1" refers to that having a polypeptide sequence with less amino acids than SEQ ID NO: 1.

It is well known in the art that the polypeptide may be modified by substituting, inserting, deleting and/or adding one or more amino acids while the enzymatic activity is maintained. For example, it is common to substitute one amino acid at a given position with a chemically equivalent amino acid without affecting the function and property of the protein. Therefore, it is anticipated that a functionally equivalent product may be produced by substituting one negatively charged residue with another or substituting one positively charged residue with another The positions of the amino acid residues modified in the amino acid sequence and the number of the amino acids modified are not particularly limited. Modification that can be introduced without affecting the protein activity can be recognized by skilled artisan.

Method for Preparing Conjugate

PEG may be covalently bound to asparaginase, alkaline phosphatase or urease through a linker by using the method known in the art, for example, the method described in PEG Chemistry:Use in Biotechnology and Biomedicine, J. M. Harris ed. (1992), which is incorporated herein by reference.

The group used for covalently binding PEG to a multimeric protein may be any of the biocompatible linkers. "Biocompatible" means that the compound or group is nontoxic and may be used in vitro or in vivo without causing damage, vomit, diseases, or death. PEG may be bound to the group, for example, through an ester bond, a thiol bond, or an amide bond.

In the present invention, the most preferred biocompatible linkers share a common feature that they are coupled to an amino group of a multimeric protein through a succinimidyl acetate group or a propionaldehyde group. Moreover, the protein may be directly conjugated to PEG through an amino group, a sulfhydryl group, a hydroxyl group, or a carboxyl group. In a most preferred embodiment, PEG is coupled to an amino group on the asparaginase, alkaline phosphatase, urease, and glutamate dehydrogenase.

In an aspect, the present invention relates to a method for preparing a conjugate, which comprises:reacting an amount of a multi-arm PEG modifier with an amount of asparaginase, alkaline phosphatase or urease in a buffer for a sufficient period of time to covalently bind PEG to the protein. In a particular embodiment, the asparaginase is derived from *E. Coli*, and more particularly, the asparaginase has an amino acid sequence as shown in SEQ ID NO: 1. In an embodiment, the PEG is 4SCM5K and 4ALD10K.

In a particular embodiment, when a propionaldehyde activated PEG is used, the buffer has a pH ranging from about 4.0 to about 9.0. Most preferably, the pH is in the range of about 5.0 to 6.0, for example, about 5.0, 5.1, 5.2, 5.3, 5.4, 5.5, 5.6, 5.7, 5.8, 5.9 or 6.0.

When a succinimidyl acetate activated PEG is used, the buffer has a pH ranging from about 6.0 to about 9.0. Most preferably, the pH is in the range of about 7.0 to 8.0, for example about 7.0, 7.1, 7.2, 7.3, 7.4, 7.5, 7.6, 7.7, 7.8, 7.9 or 8.0.

In addition, the asparaginase, alkaline phosphatase, urease, and glutamate dehydrogenase are PEGylated at a protein concentration of about 0.5-30 mg/mL, more particularly about 2-20 mg/mL, and most particularly about 3-15 mg/mL. In a particular embodiment, the PEGylated asparaginase at such protein concentrations is derived from *E. Coli*, and more particularly, the asparaginase has a sequence as shown in SEQ ID NO: 1.

At an elevated protein concentration, the PEGylation progresses rapidly and is completed in less than 3 hrs. In addition, the PEG and asparaginase, alkaline phosphatase, urease, or glutamate dehydrogenase are used at a molar ratio of at most 200:1, for example, 200:1, 150:1, 100:1, 80:1, 70:1, 60:1, 50:1, 40:1, 30:1, 20:1, 15:1, 10:1, or 5:1.

The present invention is further described with reference to examples below. However, the scope or implementations of the present invention is not limited by any examples or combinations thereof. The scope of the present invention is defined by the appended claims. The scope of the claims may be readily apparent to one skilled in the art from the descriptions and general knowledge in the art. Any modifications or changes may be made by those skilled in the art to the technical solution of the present invention without departing from the spirit and scope of the present invention, which are all contemplated in the scope of the present invention.

Example 1: Preparation and Analysis of PEG Conjugate of Asparaginase

Preparation Example 1: Preparation, Purification and Identification of the PEGylated Asparaginase According to the Present Invention 1. Preparation of PEG Conjugate Sample The asparaginase (available from Qianhong Biopharma Co., Ltd and having a sequence as shown in SEQ ID NO: 1) was dissolved in a 50 mM acetic acid-sodium acetate buffer (pH 5.0) (available from Sinopharm Group) to formulate a 8 mg/mL solution, and then modified respectively with 4PALD5K and 4PALD10K (available from Beijing Jiankai science and Technology Co. Ltd.) as a PEG modifier. The reaction was carried out at 4° C. for 12 hrs at a molar ratio of asparaginase:PEG modifier:reactant (sodium cyanoborohydride, available from Sigma) 1:50:2500, and then terminated with 1 M glycine.

Also, the asparaginase was dissolved in a 50 mM PB buffer (pH 7.5) (which was formulated with disodium hydrogen phosphate and sodium dihydrogen phosphate, and available from Sinopharm Group) to formulate a 8 mg/mL solution, and then modified respectively with 4SCM5K and 8SCM10K (available from Beijing Jiankai science and Technology Co. Ltd.) as a PEG modifier. The reaction was carried out at 4° C. for 2 hrs at a molar ratio of asparaginase:PEG modifier 1:50.

2. Purification of PEG Conjugate Sample 2.1. Removal of Unreacted PEG by Chromatography Chromatography conditions: Q ion exchange column (available from GE, HiTrap Q HP 5 mL), equilibrium buffer: 20 mM Tris-HCl (pH 8.0) (available from Sinopharm Group); elution buffer: 1 M NaCl in 20 mM Tris-HCl (pH 8.0) (available from Sinopharm Group), flow rate: 2.5 mL/min; and detection wavelength 280 nm.

Sample loading: The modified product was adjusted to pH 8.0 with a 0.5 M NaOH solution, and bound to the Q ion exchange column.

Equilibrium: The column was washed with 5 column volumes of the equilibrium buffer.

Collection: The modified product was eluted off with 50% of elution buffer, and the sample corresponding to the elution peak was collected.

2.2. Purification of Mono-Modified PEG Conjugate by Chromatography

Chromatography conditions: Hiload 16/60 Superdex 200 pg (available from GE) semi-preparative gel filtration column, elution buffer: PBS, flow rate: 1.5 mL/min, and detection wavelength 280 nm.

3. Detection of PEG Conjugate Sample by Protein Electrophoresis

The stacking gel was 5%, and the resolving gel was 7%. The stacking gel buffer was 0.5 M Tris-HCl buffer (pH 6.8) and the resolving gel buffer was 1.5 mol/L Tris-HCl buffer (pH 8.8). 10 μg of the protein sample was mixed with the sample buffer of equal volume, boiled for 5 min at 100° C., then loaded and run, and stained with Coomassie brilliant blue R250 (available from Sinopharm Group) after electrophoresis.

Figure 1:
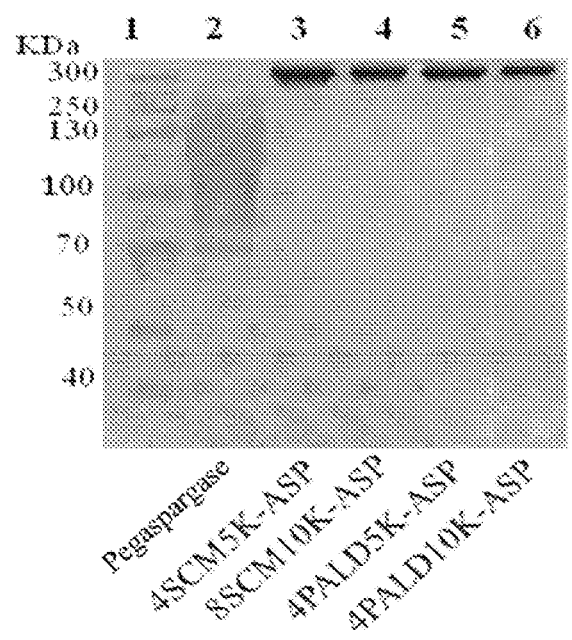
FIG. 1 shows protein electrophoresis analysis of various PEG-ASP conjugates.

It can be seen from FIG. 1 that the electrophoresis strip of the modified products 4SCM5K-ASP, 8SCM10K-ASP, 4PALD5K-ASP and 4PALD10K-ASP are highly uniform, suggesting that the 4 subunits of ASP are well conjugated. Compared with the similar product Pegaspargase (manufactured by Jiangsu Hengrui Pharmaceutical Co., Limited) available in the market, the uniformity is highly improved.

Preparation Examples 2 to 4 were the same as Preparation Example 1 except that the pH, reaction temperature, reaction time, protein concentration, and molar ratio are different. The specific parameters and yield are shown in a table below.

TABLE 1

Relevant parameters in Preparation Examples 2 to 4

| Reaction condition | Preparation Example 2 | Preparation Example 3 | Preparation Example 4 |
|---|---|---|---|
| pH | 6.0 | 7.0 | 8.5 |
| Modifier | 4PALD5K | 4SCM5K | 8SCM10K |
| Molar ratio (protein:PEG:reductant) | 1:100:5000 | 1:25 (without reductant) | 1:100 (without reductant) |

TABLE 1-continued

Relevant parameters in Preparation Examples 2 to 4

| Reaction condition | Preparation Example 2 | Preparation Example 3 | Preparation Example 4 |
|---|---|---|---|
| Reaction temperature | 25° C. | 4° C. | 37° C. |
| Reaction time (hr) | 5 | 24 | 2 |
| Protein concentration (mg/mL) | 15 | 10 | 1 |
| Yield (%) | 80 | 78 | 85 |

Example 2: Preparation and Analysis of PEG Conjugates of Alkaline Phosphatase, Urease and Glutamate Dehydrogenase Alkaline phosphatase (AKP) is an enzyme that is widely distributed in various organs of human and can dephosphorylate a corresponding substrate. AKP removes the phosphate group on the substrate molecule by hydrolyzing phosphoric acid monoester, to produce phosphate ions and free hydroxyl groups. The substrate includes nucleic acids, proteins, and alkaloids. AKP is a homologeous dimeric protein, in which each subunit has a molecular weight of 28 kDa.

The monomeric Hp urease is a hexamer composed of the subunits A and B, in which the molecular weights of the subunits A and B are about 30 kDa and 64 kDa respectively, and the ratio is 1:1. In this example, the urease used is a monomeric protein formed of the subunits A and B that cannot form a 6 mer.

Glutamate dehydrogenase can catalyze the deamination of glutamate to produce α-ketoglutarate and ammonia, and is the only enzyme that can utilize NAD+ and NADH+ as the reduction equivalent and a dehydrogenase that does not need oxygen. Glutamate dehydrogenase plays an important role in amino acid metabolism, and is an allosteric enzyme consist of 6 identical subunits, each subunit having a molecular weight of 56000.

The alkaline phosphatase (available from SIGMA), urease (available from SIGMA), and glutamate dehydrogenase (available from SIGMA) were respectively dissolved in a 50 mM PB buffer (pH 7.5) to formulate an 8 mg/mL solution, and modified respectively with SCM5K and 4SCM5K, (available from Beijing Jiankai science and Technology Co. Ltd.) as a PEG modifier. The reaction was carried out at 4° C. for 2 hrs at a molar ratio of alkaline phosphatase or urease:PEG modifier 1:50.

The preparation and analysis by electrophoresis of the modified product were the same as those in Preparation Example 1 in Example 1. The analysis results are shown in FIGS. 2a-2c. It can be seen from FIGS. 2a-2c that the uniformity of 4SCM5K-AKP, 4SCM5K-URE, and 4SCM5K-GDH is obviously better than that of SCM5K-AKP, SCM5K-URE, and SCM5K-GDH, suggesting that the subunits in AKP, URE, or GDH can be well conjugated by a 4-arm PEG modifier. The product modified with a monomethoxy PEG modifier has a poor uniformity, and the monomethoxy PEG modifier cannot serve to polymerize the subunits.

As can be seen from Examples 1 and 2, the subunits in alkaline phosphatase, asparaginase, urease, and glutamate dehydrogenase can be conjugated together by modification with a multi-arm PEG modifier, such that the uniformity of the modified product is obviously improved. The alkaline phosphatase and urease are a protein composed of two subunits, the asparaginase is a protein composed of four subunits, and the glutamate dehydrogenase is a protein composed of 6 subunits. Therefore, the multi-arm PEG modifier is useful in the modification of proteins containing multiple subunits, and can conjugate the subunits compared with the monomethoxy PEG modifier, thereby improve the uniformity of the modified product.

Example 3: Thermal Stability Study of PEG Conjugates of Alkaline Phosphatase, Urease, and Glutamate Dehydrogenase To compare the stability of alkaline phosphatase, urease, and glutamate dehydrogenase modified with a monomethoxy PEG modifier and with a multi-arm PEG modifier, the changes in activity of the modified products 4SCM5K-AKP, 4SCM5K-URE, 4SCM5K-GDH, SCM5K-AKP, SCM5K-GDH, and SCM5K-URE obtained in Example 2 after standing in a water bath at 60° C. for a period of time were detected in this example, to investigate the difference in stability therebetween. The method was specifically as follows. The sample dissolved in a PBS buffer at a protein concentration of 1 mg/mL was placed in a water bath at 60° C., sampled periodically and stored in a freezer at 4° C. for use. The activity was determined after the sampling was completed, to evaluate the stability according to the changes in activity. The results are shown in FIGS. 3a-3c.

It can be seen from FIG. 3a that the stability of 4SCM5K-AKP is obviously better than that of SCM5K-AKP. After standing in the water bath at 60° C. for 120 min, the 4SCM5K-AKP retains 70% of the activity, and the activity of SCM5K-AKP declines to about 40%. At 400 min, the 4SCM5K-AKP retains about 60% of the activity, and the activity of SCM5K-AKP is substantially completely lost, suggesting that after the subunits in AKP are conjugated with a multi-arm PEG, the stability of AKP is better than the product modified with a conventional monomethoxy PEG. Also, it can be seen from FIG. 3b that the stability of 4SCM5K-URE is obviously better than that of SCM5K-URE. After standing in the water bath at 60° C. for 120 min, the 4SCM5K-URE still retains 400/% of the activity, and the activity of SCM5K-URE is substantially completely lost, suggesting that after the subunits in URE are conjugated with a multi-arm PEG, the stability of URE is better than that of a product modified with a conventional monomethoxy PEG. Therefore, the stability of a protein composed of two subunits after being conjugated with a multi-arm PEG is better than that of a product conjugated with a monomethoxy PEG. Similarly, the activity of 4SCM5K-GDH and SCM5K-GDH at 0.5 hr is compared, and a similar result is obtained. Therefore, the stability of a protein composed of 6 subunits after being conjugated with a multi-arm PEG is better than that of a product conjugated with a monomethoxy PEG. Accordingly, it can be reasonably assumed that the stability of a multimeric protein after modification with a multi-arm PEG is better than that of a product modified with a conventional monomethoxy PEG.

Example 4: In-Vitro Activity Detection of PEG-ASP Conjugate

The amido group on asparagine can be hydrolyzed by asparaginase. Based on this principle, the activity of asparaginase was determined. The specific determination method was as described in *Pharmacopoeia of People's Republic of China* (2005 Edition), Part II, Page 31. The reagents needed were all available from Sinopharm Group Chemical Reagent Co., Ltd. The detected samples were respectively 4SCM5K-ASP, 8SCM10K-ASP, 4PALD5K-ASP, 4PALDIOK-ASP and unmodified original protein as well as similar product Pegaspargase (manufactured by Jiangsu Hengrui Pharmaceutical Co., Limited) available in the market. The results of comparison of their relative activity are shown in FIG. 4.

As can be seen from the activity determination results shown in FIG. 4, the activities of the PEG modified asparaginase according to the present invention and the similar product Pegaspargase available in the market are decreased to some extent. However, the PEG modified asparaginase according to the present invention retains about 80% of the activity of the original protein, and the activity of Pegaspargase declines dramatically, with only about 50% of the activity being retained.

It can be concluded through comparison that the activity of the modified products 4SCM5K-ASP, 8SCM10K-ASP, 4PALD5K-ASP, and 4PALDIOK-ASP is higher than that of Pegaspargase.

Example 5: Thermal Stability Study of PEG-ASP Conjugate

To confirm that PEG modification can increase the stability of asparaginase and compare with the stability of Pegaspargase, the activity of the modified products 4SCM5K-ASP, 8SCM10K-ASP, 4PALD5K-ASP, and 4PALD10K-ASP obtained in Example 1 and the original protein as well as Pegaspargase after standing in a water bath at 37° C. for a period of time were detected in this example. The method was specifically as follows. The sample dissolved in a PBS buffer at a protein concentration of 1 mg/mL was placed in a water bath at 37° C., sampled periodically and stored in a freezer at 4° C. for use. The bioactivity was determined after the sampling was completed. The determination results are shown in FIG. 5.

As can be seen from the activity determination result, the activity of the original protein decreases significantly at 25 hrs, and is completely lost after 48 hrs. The stability of Pegaspargase is better than that of the original protein; however, the activity begins to decrease after 75 hrs, and is completely lost at 120 hrs. In contrast, the stability of the products 4SCM5K-ASP, 8SCM10K-ASP, 4PALD5K-ASP, and 4PALD10K-ASP modified with a multi-arm PEG provided in the present invention is better, and the activity decreases slowly, where the activities of 4SCM5K-ASP and 8SCM10K-ASP substantially have no change.

Therefore, the stabilities of 4SCM5K-ASP, 8SCM10K-ASP, 4PALD5K-ASP, and 4PALD10K-ASP prepared in the present invention are all far greater than that of Pegaspargase.

It can be known from the results in Examples 3, 4, and 5 that the stability of a product obtained by modifying a protein composed of multiple subunits with a multi-arm PEG is better than that of a product modified with a conventional monomethoxy PEG.

The multi-arm PEG used in the present invention is suitable for use in modification of all the proteins composed of multiple subunits, and the disassociation of the subunits is prevented by greatly increasing the stability by covalently conjugating the subunits, thereby reducing the activity loss and production of immunogenicity resulting therefrom.

Example 6: Study on Stability of the Conjugated Group in PEG-ASP Conjugate

The stability of the original protein can be enhanced by a PEG modifier. However, depending on different conjugated groups, detachment of PEG may occur due to the degradation of the conjugated groups, thus affecting the stability and bioactivity of the drugs. To compare the stability of PEG-ASP conjugate according to the present invention with the commercially available Pegaspargase, the detachment of PEG from 4SCM5K-ASP and Pegaspargase after standing in a water bath at 37° C. for a period of time were detected. The method was specifically as follows. The sample dissolved in a PBS buffer at a protein concentration of 1 mg/mL was placed in a water bath at 37° C., sampled periodically and stored in a freezer at 4° C. for use. Protein electrophoresis was done after the sampling was completed, followed by staining PEG-ASP conjugate with iodine. The detection results are shown in FIGS. 6a-6b.

It can be seen from FIG. 6a that the Pegaspargase sample contains free PEG, suggesting that the detachment of PEG occurs before the stability study, and is further exacerbated with the elapse of time. It can be seen from FIG. 6b that no detachment of PEG occurs for 4SCM5K-ASP throughout the study, suggesting that the stability of the covalent bond formed between the conjugated PEG and the amino group of the protein is very good, and significantly better than that of Pegaspargase. The PEG modified protein drugs are generally in the form of injections, and the antigenic determinant of the protein is exposed if the detachment of PEG occurs in vivo, causing significant immunogenicity and thus leading to the decrease in therapeutic efficacy and the production of side effect.

It can be known from the experimental result that the protein drugs modified with a multi-arm PEG have a high stability, and is unsusceptible to PEG detachment, thereby increasing the stability of the modified product and reducing the occurrence probability of immunogenicity caused by the drugs.

Example 7: Analysis of PEG-ASP Conjugate and Original Protein by Circular Dichroism Spectroscopy The secondary and tertiary structures of a unmodified and modified protein are characterized by circular dichroism spectroscopy. The protein concentrations ranged from 0.1 to 0.2 mg/mL. The sample was charged into a circular dichroism cuvette of 1 mm optical path, and detected for its circular dichroism spectra in a far ultraviolet region (190 nm-250 nm) and a near ultraviolet region (253 nm-480 nm), at a scanning bandwidth of 1 nm and a scanning speed of 500 nm/min. A corresponding buffer was used as the background in each detection, and there measurements were averaged. As can be seen from FIGS. 7a-7b, the circular dichroism spectrum in the far ultraviolet region of the PEG-ASP conjugate has almost no peak shift, as compared with that of the original protein.

However, the peak value varies to some degree, which may be attributed to the influence of PEG modification on the absorbance. The spectrum of the PEG-ASP conjugate is substantially overlapped with that of Pegaspargase, suggesting that no difference exists in the secondary structure after modification with different modifiers. This result is in accord with the PEG property. PEG in solution is a flexible amphiphilic polymer, and has no obvious influence on the protein structure after conjugating to the protein surface. Therefore, the PEG modification has no influence on the secondary structure of ASP. Likewise, the circular dichroism spectrum in the near ultraviolet region of the PEG-ASP conjugate has almost no peak shift, as compared with that of the original protein. The peak value varies to some degree, but is substantially overlapped with that of Pegaspargase, suggesting that the PEG modification has no influence on the tertiary structure of ASP. In general, the advanced structure of ASP substantially has no change for the conjugates prepared with various modifiers. After modification with PEG, the structure is unchanged and thus the loss of activity of the conjugate is small compared with activity of the original protein.

Example 8: Comparison of Inhibition of Various PEG-ASP Conjugates on Different Tumor Cells To evaluate the inhibition of PEG-ASP conjugates on tumor cells, and compare with that of Pegaspargase, THP-1 (derived from human monocytic leukemia cell line), U937 (derived from human monocytic leukemia cell line), Raji (derived from human lymphoma cell line), Jurkat (derived from human acute T cell leukemia cell line), L1210 (derived from mouse leukemia cell), and L5178Y (derived from mouse lymphoma cell) were used for evaluation. The inhibition on cells was tested by the MTT method, and the inhibition rate at different concentrations dosed was investigated, to finally calculate the $IC_{50}$ value. The calculation results are shown in Table 2.

TABLE 2

$IC_{50}$ values of various PEG-ASP conjugates and Pegaspargase for tumor cells

|  | ASP | Pegaspargase | 4SCM5K-ASP | 4PALD10K-ASP |
| --- | --- | --- | --- | --- |
| THP-1 | 0.87 μmol/L | 0.78 μmol/L | 0.54 μmol/L | 0.13 μmol/L |
| U937 | 0.05 μmol/L | 0.18 μmol/L | 0.0004 μmol/L | 0.06 μmol/L |
| Raji | 5.3 μmol/L | 2.7 μmol/L | 3.6 μmol/L | 0.8 μmol/L |
| Jurkat | 4.9 μmol/L | 2.4 μmol/L | 0.1 μmol/L | 0.2 μmol/L |
| L1210 | 1.26 μmol/L | 1.92 μmol/L | 1.5 μmol/L | 0.44 μmol/L |
| L5178Y | 8.6 μmol/L | 2.7 μmol/L | 3.03 μmol/L | 2.1 μmol/L |

As can be known from the experimental result, the asparaginase modified with a multi-arm PEG provided in the present invention has a killing effect for the above 6 tumor cells that is generally higher than that of the unmodified asparaginase. The 4SCM5K-ASP and 4PALDIOK-ASP provided in the present invention has an anti-tumor activity that is obviously higher than that of pegaspargase, and exhibits a good anti-tumor effect on numerous cell lines. Particularly. 4PALD10K-ASP has a lowest $IC_{50}$ and thus the highest anti-tumor activity for the numerous cell lines.

Example 9: In-Vitro Inhibitory Effect of Various PEG-ASP Conjugates on Tumors 40 female nude mice (BALB/cA-nu) aged 4-6 weeks and weighed 15-18 g were designated to 5 groups, including a Pegaspargase group, an ASP group, PBS group, a 4PALD10K-ASP group, and a 4SCM10K-ASP group, and each group having 8 animals. Before experiment, the weights of the mice were recorded and the liver functions were detected. At the start of the test, each of the nude mice was intraperitoneally injected with 100 mg/kg of cyclophosphamide for consecutive 4 days, and with $5 \times 10^6$ tumor cell L1210 at the Day 5. The animals were administered once on the following day by intramuscularly injecting 4.7 mg/kg of Pegaspargase, ASP, PBS, 4PALDIOK-ASP, and 4SCM10K-ASP. The tumor inhibition rate was calculated 3 and 6 days after injection. The experimental results are shown in FIG. 8 and Table 3.

TABLE 3

Influence of PEG modified products on tumor inhibition rate in mice inoculated with tumor cells

|  |  | Tumor inhibition rate (%) | |
| --- | --- | --- | --- |
| Group | Number of animals | d3 | d6 |
| Model group | 8 | / | / |
| ASP | 8 | 7.1 | 32.9 |
| Pegaspargase | 8 | 19.9 | 35.5 |
| 4PALD10K-ASP | 8 | 36.3 | 40.0 |
| 4SCM10K-ASP | 8 | 37.6 | 43.5 |

It can be seen from FIG. 8 and Table 3 that the inhibition rate on tumor of the Pegylated asparaginase is obviously higher than that of unmodified asparaginase, and the inhibition rate of the asparaginase group on Days 3 and 6 is lower than that of other PEG modified product groups. In addition, the tumor inhibition rates, and especially the tumor inhibition rate on d3 of the 4PALD10K-ASP and 4SCM10K-ASP groups are better than that of the Pegaspargase group, suggesting that the therapeutic efficacy of the asparaginase modified with a multi-arm PEG is better than the asparaginase modified with a conventional monomethoxy PEG modification. This may correlate with the high stability of 4PALD10K-ASP and 4SCM10K-ASP. This example preliminarily indicates that the inhibitory effect on tumor of 4SCM10K-ASP and 4PALD10K-ASP is superior to that of the similar product Pegaspargase available in the market.

Example 10: Immunogenicity of PEG-ASP Conjugate

The structural specificity of the PEG molecule can reduce or abolish the ability to induce to produce neutralizing antibody and to bind to the antibody, such that it is difficult to be recognized and cleared by the immune system. Therefore, the immunogenicity of the PEG modified protein can be reduced to some degree.

In this example, the relative immunogenicity of various PEG-ASP conjugates in mice was determined, and compared with that of the original protein and Pegaspargase. The test included a 4PALDIOK-ASP group, a 4SCM5K-ASP group, a Pegaspargase group and an original protein group. The mice were injected with 2 mg/kg of the above products (based on the weight of the protein) at the tail vein once every two weeks for consecutive 8 weeks. Blood was taken from the orbit 1 week after administration. The level of the anti-asparaginase antibody in serum was measured by indirect ELISA (in which the secondary antibody used was available from SIGMA). The results are shown in FIG. 9.

As can be known from the results, the antibody titer in the mice in the 4PALDIOK-ASP and 4SCM5K-ASP group is far lower than that in the mice in the original protein and Pegaspargase group, suggesting that the immunogenicity of the protein after PEG modification can be obviously reduced. The subunits are well conjugated since the proteins are modified with a multi-arm PEG in the 4PALD10K-ASP and 4SCM5K-ASP group. Therefore, degradation is unlikely to occur in vivo, thus causing no immune reaction. Although Pegaspargase is also modified with PEG, the subunits are not well conjugated, and the molecular stability is low. The disassociation of subunits may easily occur in vivo, thus exposing the epitope, and causing an immune reaction.

Example 11: Pharmacokinetic Study of PEG-ASP Conjugate

The steric hinderance of PEG allows the resistance of the modified protein to degradation by a protease to be greatly improved, and the volume for molecular exclusion of the modified protein is obviously increased, such that the renal filtration and clearance rate is significantly reduced, thereby improving the in-vivo half-life of the original protein.

In this example, the blood concentration of the PEG modified asparaginase was studied by the $^{125}$I isotope tracing method. To reduce the absorption of the labeled drug by the thyroid gland of the rats, 1 mL of 1% KI solution was intraperitoneally injected about 8 hrs before experiment to saturate the thyroid gland of the rats. The rats (female:male 1:1) were designated to a 4SCM5K-ASP group and a Pegaspargase group, each group having 8 animals. The specific operations were as follows.

1. The hydroxyl group on the phenyl ring of the amino acid residue in the protein molecule was substituted with radioactive iodine, to obtain an $^{125}$I labeled protein that can be radioactively traced.
2. The rats were numbered with picric acid on their body according to the numbering rule and weighed. The rats were immobilized with a fixture, and then administered by injection at the tail vein (1.5 U/kg). After administration, the rats were released, and allowed to move freely and access to water and food ad libitum.
3. About 0.2 mL of blood was taken from the orbit 1 min, 5 min, 10 min, 20 min, 30 min, 60 min, 3 hrs, 6 hrs, 12 hrs, 24 hrs, 48 hrs, 84 hrs, 96 hrs, 144 hrs, 168 hrs, 192 hrs, 216 hrs, and 264 hrs after administration, and added with EDTA for anticoagulation.
4. The rat plasma was isolated by centrifugation at 5000 rpm for 3 min, and the radioactivity of the plasma was measured by using a gamma counter (Anke Zhongjia, GC-911), in which the measurement time was 1 min.
5. After the radioactivity was measured, the plasma was recovered and the undegraded proteinogenous drug was separated by HPLC (Shimadzu LC-20AT), HPLC. After animal experiment, the blood drug concentration in SD rats at each time point can be obtained after data processing. The pharmacokinetic parameters of the drug are calculated by the pharmacokinetic software DAS from the time and corresponding blood drug concentration.

The experimental results show that the pharmacokinetic model of Pegaspargase and 4SCM5K-ASP is a three-compartment model. The calculation result of each parameter is shown in Table 4.

TABLE 4

| Comparison of pharmacokinetic parameters of PEG-ASP conjugate and Pegaspargase | | | |
|---|---|---|---|
| Sample | T½γ (h) | AUC (mg/L*h) | CL (L/h/kg) |
| Pegaspargase | 25.12 | 459 | 0.028 |
| 4SCM5K-ASP | 45.90 | 805 | 0.015 |

Compared with Pegaspargase, the half-life of 4SCM5K-ASP is obviously extended from about 25 hrs to 45 hrs and area under curve (AUC) is significantly increased from 459 mg/L*h to 805 mg/L*h. Moreover, the clearance rate of 4SCM5K-ASP from blood is also lower than that of Pegaspargase. Therefore, compared with Pegaspargase, the asparaginase modified with a multi-arm PEG has an obviously enhanced in-vivo stability, the half-life is greatly increased, and the metabolic rate in blood is obviously reduced, such that the efficacy lasting time of the drug is effectively extended. It can be reasonably inferred that the stability of the asparaginase modified with a multi-arm PEG used in the present invention is increased due to the enhanced interaction between the subunits of the protein, which is also confirmed by the pharmacokinetic test. Because the activating group on the 4SCM10K-ASP is the same as that on the 4SCM5K-ASP and the PEG chain is much longer, the half-life for the 4SCM10K-ASP group is presumed to be greatly higher than 45.90 hrs based on the data obtained from the 4SCM5K-ASP group, the AUC is much higher, and thus the pharmacokinetic data is obviously better than that of the 4SCM5K-ASP.

What is claimed is:

1. A multimeric protein modified with a multi-arm polyethylene glycol (PEG), the multi-arm polyethylene glycol comprising a chain of repeating units having from 2 to 16 activating groups that react with respective amino acid residues of subunits of the multimeric protein, wherein the activating groups enhance interaction between the subunits such that the multimeric protein modified with the multi-arm PEG has increased stability and reduced immunogenicity as compared with the multimeric protein when modified with a PEG comprising a chain having only 1 of the activating groups.

2. The multimeric protein modified with a multi-arm PEG according to claim 1, wherein the multi-arm PEG is selected from the group consisting of:

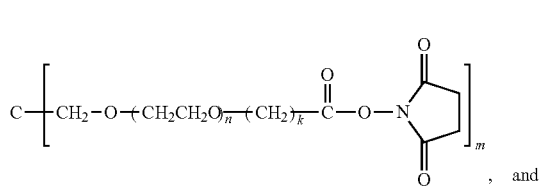

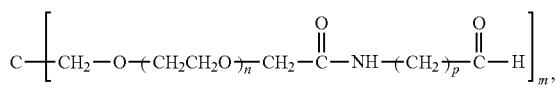

wherein n is an integer from 1 to 2000; k is 1 or 2; m is an integer from 2 to 16; p is an integer from 1 to 4; and the molecular weight of the multi-arm PEG is from 1 to 100 kDa.

3. The multimeric protein modified with a multi-arm PEG according to claim 2, wherein n is an integer from 2 to 500, k is 1, m is 4, and p is 2; and the molecular weight of the multi-arm PEG is from 1 to 40 kDa.

4. The multimeric protein modified with a multi-arm PEG according to claim 3, wherein the multi-arm PEG is an aldehyde or ester activated multi-arm PEG derivative, wherein the ester activated PEG derivative is selected from the group consisting of 4-arm PEG succinimidyl acetate, 4-arm PEG succinimidyl propionate and 4-arm PEG succinimidyl carbonate; and the aldehyde activated PEG derivative is selected from the group consisting of 4-arm PEG propionaldehyde, 4-arm PEG butyraldehyde, 4-arm PEG acetaldehyde and 4-arm PEG amylic aldehyde.

5. The multimeric protein modified with a multi-arm PEG according to claim 2, wherein the multimeric protein is selected from the group consisting of alkaline phosphatase, asparaginase and urease.

6. The multimeric protein modified with a multi-arm PEG according to claim 1, which is obtained by a method comprising the steps of:
(1) mixing a protein to be modified, and a PEG modifier at a ratio, and subjecting them to modification in a buffer;
(2) after the modification is completed, removing the PEG modifier in the modified product that is unreacted with the protein by ion exchange chromatography; and
(3) purifying the modified product by gel filtration chromatography, to collect the modified product of interest; wherein the PEG modifier is selected from the group consisting of:

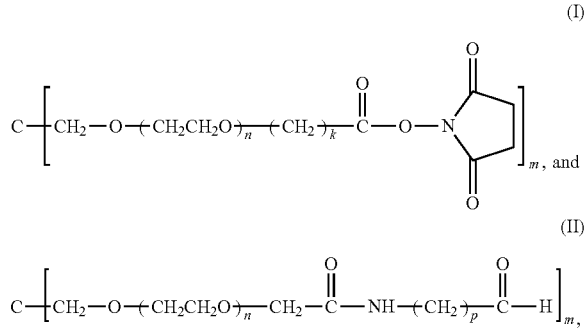

wherein n is an integer from 1 to 2000; k is 1 or 2; m is an integer from 2 to 16; p is an integer from 1 to 4; and the molecular weight of the multi-arm PEG is from 1 to 100 kDa.

7. The multimeric protein modified with a multi-arm PEG according to claim 1, which is an asparaginase modified with the multi-arm PEG.

8. A pharmaceutical composition comprising the asparaginase modified with a multi-arm PEG according to claim 7 and a pharmaceutically acceptable adjuvant, wherein the dosage form of the pharmaceutical composition is an injectable lyophilized powder.

9. The multimeric protein modified with a multi-arm PEG according, to claim 1, wherein the multi-arm PEG has the following structure:

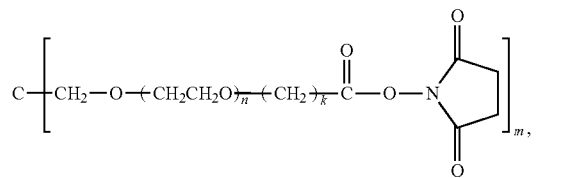

wherein n is an integer from 1 to 2000; k is 1 or 2; m is, an integer from 2 to 16; and the molecular weight of the multi-arm PEG is from 1 to 100 kDa.

10. The multimeric protein modified with a multi-arm PEG according to claim 9, wherein the multimeric protein is alkaline phosphatase, asparaginase or urease, and the multi-arm PEG is selected from the group consisting of 4-arm PEG succinimidyl acetate, 4-arm PEG succinimidyl propionate and 4-arm PEG succinimidyl carbonate.

11. The multimeric protein modified with a multi-arm PEG according to claim 10, wherein the multimeric protein is asparaginase and the multi-arm PEG is 4-arm PEG succinimidyl acetate.

12. The multimeric protein modified with a multi-arm PEG according to claim 1, wherein the multi-arm PEG has the following structure:

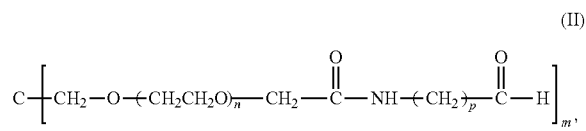

wherein n is an integer from 1 to 2000; m is an integer from 2 to 16; p is an integer from 1 to 4; and the molecular weight of the multi-arm PEG is from 1 to 100 kDa.

13. The multimeric protein modified with a multi-arm PEG according to claim 12, wherein the multimeric protein is alkaline phosphatase, asparaginase or urease, and the multi-arm PEG is selected from the group consisting of 4-arm PEG propionaldehyde, 4-arm PEG butyraldehyde, 4-arm PEG acetaldehyde and 4-arm PEG amylic aldehyde.

14. The multimeric protein modified with a multi-arm PEG according to claim 13, wherein the multimeric protein is asparaginase and the multi-arm PEG is 4-arm PEG propionaldehyde.

15. A method for making the multimeric protein modified with a multi-arm polyethylene glycol (PEG) according to claim 1, comprising the steps of:
(1) mixing a protein to be modified and a PEG modifier at a ratio, and subjecting them to modification in a buffer;
(2) after the modification is completed, removing the PEG modifier in the modified product that is unreacted with the protein by ion exchange chromatography; and
(3) purifying the modified product by gel filtration chromatography, to collect the modified product of claim 1; wherein the PEG modifier is selected from the group consisting of:

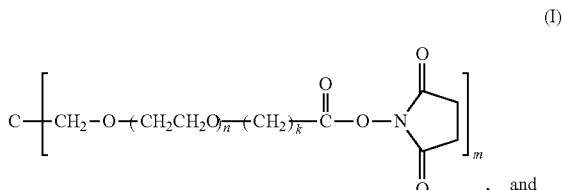

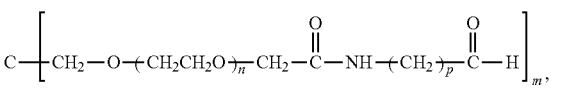

wherein n is an integer from 1 to 2000; k is 1 or 2; m is an integer from 2 to 16; p is an integer from 1 to 4; and the molecular weight of the multi-arm PEG is from 1 to 100 kDa.

16. The method according to claim 15, wherein n is an integer from 2 to 500, k is 1, m is 4, and p is 2; and the molecular weight of the multi-arm PEG is from 1 to 40 kDa.

17. The method according to claim 16, wherein the multi-arm PEG is an aldehyde or ester activated multi-arm PEG derivative, wherein the ester activated PEG derivative is selected from the group consisting of 4-arm PEG succinimidyl acetate, 4-arm PEG succinimidyl propionate and 4-arm PEG succinimidyl carbonate; and the aldehyde activated PEG derivative is selected from the group consisting of 4-arm PEG propionaldehyde, 4-arm PEG butyraldehyde, 4-arm PEG acetaldehyde and 4-arm PEG amylic aldehyde.

18. The method according to claim 17, wherein the multimeric protein is alkaline phosphatase, asparaginase or urease.

19. A method for treating a tumor comprising administering to a patient in need thereof a drug or pharmaceutical composition comprising the asparaginase modified with a multi-arm PEG according to claim 7.

* * * * *